US010075628B2

(12) United States Patent
Maruyama et al.

(10) Patent No.: US 10,075,628 B2
(45) Date of Patent: Sep. 11, 2018

(54) IMAGING APPARATUS AND INTRAORAL CAMERA

(71) Applicant: RF CO., LTD., Nagano (JP)

(72) Inventors: Jiro Maruyama, Nagano (JP); Yusuke Yabana, Nagano (JP); Akio Koyanagi, Nagano (JP); Chihiro Komamura, Nagano (JP); Akio Sunohara, Nagano (JP)

(73) Assignee: RF CO., LTD, Nagano (JP)

( * ) Notice: Subject to any disclaimer, the term of this patent is extended or adjusted under 35 U.S.C. 154(b) by 156 days.

(21) Appl. No.: 15/076,896

(22) Filed: Mar. 22, 2016

(65) Prior Publication Data

US 2016/0330365 A1 Nov. 10, 2016

(30) Foreign Application Priority Data

May 7, 2015 (JP) .................................. 2015-094735

(51) Int. Cl.
*H04N 5/232* (2006.01)
*H04N 5/225* (2006.01)
(Continued)

(52) U.S. Cl.
CPC ....... *H04N 5/23212* (2013.01); *A61B 1/0002* (2013.01); *A61B 1/00006* (2013.01); *A61B 1/00188* (2013.01); *A61B 1/045* (2013.01); *A61B 1/24* (2013.01); *G03B 3/10* (2013.01); *G03B 15/14* (2013.01); *H04N 5/2254* (2013.01); *H04N 5/2256* (2013.01); *H04N 2005/2255* (2013.01)

(58) Field of Classification Search
CPC ................................................. H04N 5/23212
See application file for complete search history.

(56) References Cited

U.S. PATENT DOCUMENTS

2008/0297922 A1* 12/2008 Lule .......................... G02B 7/08
359/824
2014/0368724 A1* 12/2014 Zhang .................. H04N 5/2257
348/345

(Continued)

FOREIGN PATENT DOCUMENTS

JP          2012-75690         4/2012
JP          2012075690 A  *    4/2012

*Primary Examiner* — Tung Vo
*Assistant Examiner* — Rowina Cattungal
(74) *Attorney, Agent, or Firm* — Wenderoth, Lind & Ponack, L.L.P.

(57) ABSTRACT

An imaging apparatus includes a lens, a moving mechanism, an imaging device, and a controller. The moving mechanism moves the lens in the optical axis direction. The controller drives, in response to an input of an imaging instruction, the moving mechanism to move the lens to a plurality of imaging positions from one of infinity and close-up ends to the other and drives the imaging device when the lens is positioned at each of the imaging positions. Since the interior of an oral cavity, for example, is difficult to capture, the focus can hardly be adjusted on it with high accuracy when an autofocus mechanism is used. However, since the lens is moved to the plurality of imaging positions in the optical axis direction in response to each input of the imaging instruction to obtain captured images, an in-focus image can be reliably obtained.

16 Claims, 9 Drawing Sheets

(51) Int. Cl.
    *A61B 1/24*     (2006.01)
    *A61B 1/00*     (2006.01)
    *A61B 1/045*    (2006.01)
    *G03B 3/10*     (2006.01)
    *G03B 15/14*    (2006.01)

(56) References Cited

U.S. PATENT DOCUMENTS

2016/0062134 A1* 3/2016 Sengoku ............ H04N 5/23258
                                                    348/208.7
2016/0112612 A1* 4/2016 Kakkori ............... H04N 5/2254
                                                    348/373
2016/0295097 A1* 10/2016 Shanmugavadivelu .....................
                                                    H04N 5/2254

* cited by examiner (A)

(B)

IMAGING APPARATUS AND INTRAORAL CAMERA

BACKGROUND OF THE INVENTION

1. Field of the Invention

The present invention relates to an imaging apparatus and an intraoral camera.

2. Description of the Related Art

An intraoral camera that captures an image of the interior of the oral cavity of a patient is known (see, for example, Patent Literature 1). In the intraoral camera according to Patent Literature 1, the distal end of a body case is inserted into the oral cavity of the patient. Light from an object within the oral cavity enters the body case from an imaging window provided at the distal end of the body case. The light is guided to an imaging device provided within the central portion of the body case via an optical system. Within the central portion of the body case, a focusing lens and an autofocus mechanism are provided upstream of the imaging device. According to Patent Literature 1, the autofocus mechanism moves the focusing lens in the optical axis direction to carry out focusing.

PRIOR ART REFERENCES

Patent Literature 1: Japanese Patent Application Laid-Open No. 2012-75690

Unfortunately, Patent Literature 1 poses the following problems. That is, the use of the autofocus mechanism leads to a large, heavy optical system for imaging. This makes the intraoral camera hard to use.

SUMMARY OF THE INVENTION

It is an object of the present invention to provide an imaging apparatus and an intraoral camera that can miniaturize an optical system for imaging and reduce the weight thereof.

A first aspect of the present invention is an imaging apparatus including a lens that focuses light from an object, a moving mechanism that moves the lens in an optical axis direction, an imaging device that captures an image of the object formed by the lens to obtain a captured image, and a controller for driving, in response to an input of an imaging instruction, the moving mechanism to move the lens to a plurality of imaging positions from one of infinity and close-up ends to the other and driving the imaging device when the lens is positioned at each of the imaging positions.

Since the interior of an oral cavity, for example, is difficult to capture, the focus can hardly be adjusted on it with high accuracy when an autofocus mechanism is used. However, according to the present invention, since the lens is moved to the plurality of imaging positions in the optical axis direction in response to each input of an imaging instruction to obtain captured images, an in-focus image can be reliably obtained. The imaging apparatus may store the obtained, captured image in the memory or transmit it to an external device.

According to the present invention, since an autofocus mechanism is omitted, a compact, lightweight optical system for imaging can be obtained. Further, according to the present invention, a compact optical system for imaging can be provided, thus increasing the positional degree of freedom of the optical system for imaging in the imaging apparatus.

In the present invention, the moving mechanism may include a magnet that is located outside the lens in a radial direction and moves together with the lens, a vibrating plate that supports the magnet and the lens, and generates a restoring force in a direction to return the magnet and the lens to a home position in accordance with the amount of shift of the magnet and the lens from the home position in the optical axis direction, and a coil that is located outside the magnet in the radial direction and generates a magnetic force to move the magnet and the lens in the optical axis direction upon power supply. The controller may change the amount of power supplied to the coil, to move the magnet and the lens to the plurality of imaging positions.

When the coil is located on the lens side and the magnet surrounds the coil and the lens, the coil must be wired inside the magnet. This complicates the structure of the moving mechanism.

According to the present invention, the magnet is located on the lens side and the coil surrounds the magnet and the lens. Hence, the coil can be wired outside the moving mechanism and this can simplify the structure of the moving mechanism.

In the present invention, the controller may move the lens to the plurality of imaging positions, the number of which is equal to the frame rate of the imaging device, from one of the infinity and close-up ends to the other in response to the input of the imaging instruction.

According to the present invention, imaging requires 1 sec. or less for every imaging position in one imaging instruction. Hence; the speed of the imaging operation of the imaging apparatus can be kept high enough to release user's stress.

In the present invention, the imaging apparatus may include a memory that stores the image captured when the lens is positioned at each of the imaging positions. The controller may assign as metadata a number corresponding to the imaging position of the lens to the image captured at each of the imaging positions.

According to the present invention, the captured images can be easily managed.

A second aspect of the present invention is an intraoral camera including a lens for focusing light from an object, a moving mechanism for moving the lens in an optical axis direction, an imaging device for capturing an image of the object formed by the lens to obtain a captured image, a memory for storing the captured image, a controller for driving, in response to an input of an imaging instruction, the moving mechanism to move the lens to a plurality of imaging positions from one of infinity and close-up ends to the other and stores, in the memory, the image captured when the lens is positioned at each of the imaging positions, and a case that extends in a first direction, for accommodating the lens, the moving mechanism, the imaging device, the memory, and the controller. The lens, the moving mechanism, and the imaging device are arranged to match the optical axis direction with a direction perpendicular to the first direction within a distal end of the case in the first direction.

According to the present invention, an optical system for imaging including a lens, a moving mechanism, and an imaging device is positioned on the distal end side of the intraoral camera in the first direction. Hence, a battery can be positioned on the proximal end side of the intraoral camera in the first direction to achieve wireless communication by the intraoral camera. Further, according to the second aspect, since the optical system for imaging is positioned to match the optical axis direction with a direction perpendicular to the first direction, the use of the intraoral camera can be facilitated.

DETAILED DESCRIPTION OF THE PREFERRED EMBODIMENT

Embodiments will be described below with reference to the accompanying drawings.

(First Embodiment)

Figure 1:
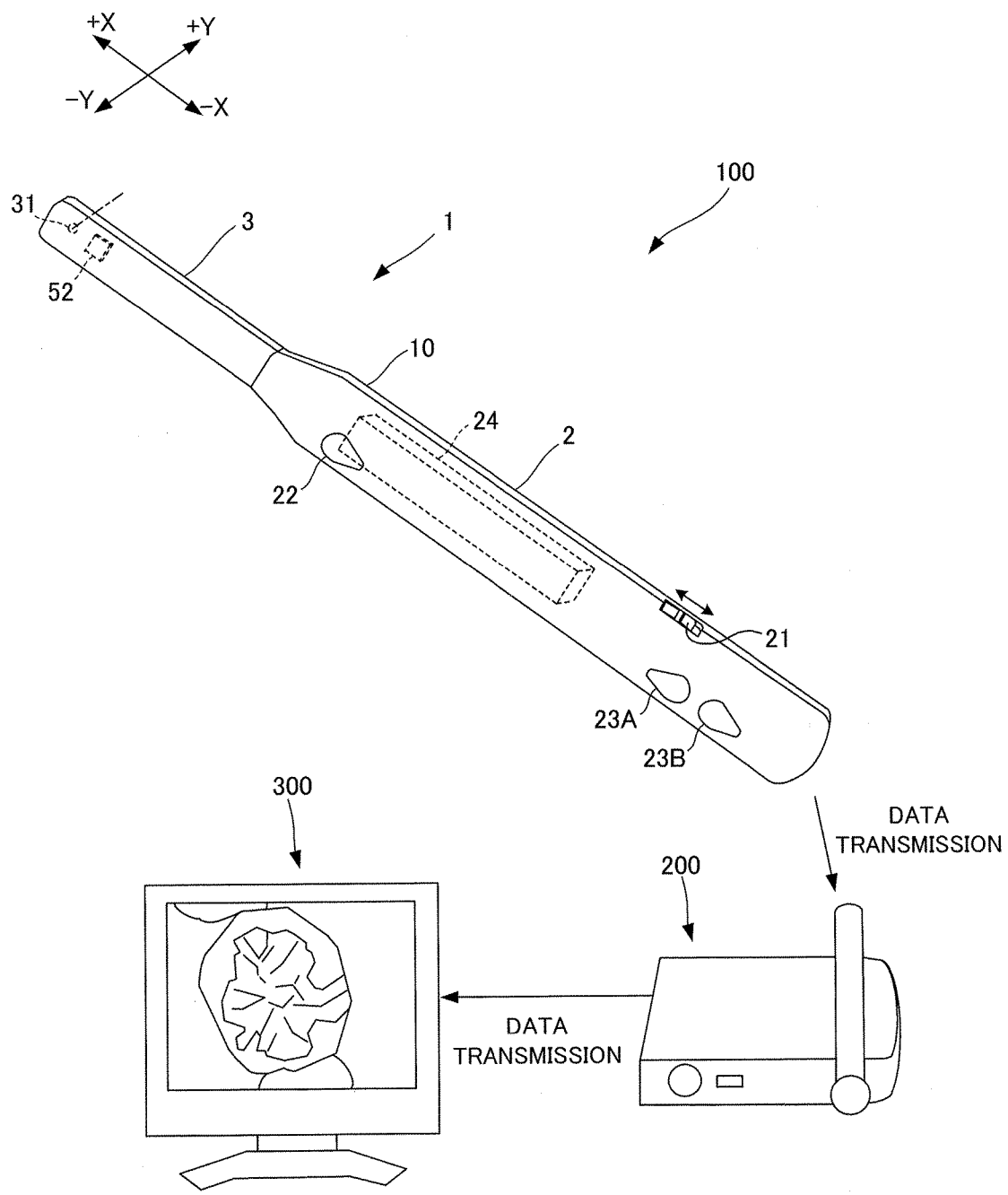
FIG. 1 is a diagram illustrating an intraoral imaging system.

FIG. 1 is a diagram illustrating an intraoral imaging system 100.

The intraoral imaging system 100 includes an intraoral camera 1 (imaging apparatus), a relay device 200, and an external device 300.

The intraoral camera 1 captures an image of an object such as a row of teeth in an oral cavity. The intraoral camera 1 communicates with the relay device 200 by radio to transmit the captured image to the external device 300 via the relay device 200.

The intraoral camera 1 includes a case 10 extending in the X direction.

The case 10 includes a gripping portion 2 extending in the X direction, and an insertion portion 3 which extends in the X direction from one end of the gripping portion 2 and is narrower than the gripping portion 2. In the following description, the X direction is defined to be negative toward the gripping portion 2 and positive toward the insertion portion 3. The gripping portion 2 has an almost cylindrical outer shape. The insertion portion 3 has an almost rectangular parallelepiped outer shape.

The insertion portion 3 is inserted into an oral cavity. An imaging window 31 is provided at the distal end of the insertion portion 3. The imaging window 31 opens in the Y direction perpendicular to the X direction. The intraoral camera 1 captures an image of the object via the imaging window 31. In the following description, the Y direction is defined to be positive from the inside of the intraoral camera 1 to the outside and negative from the outside of the intraoral camera 1 to the inside. The insertion portion 3 accommodates a memory 52. The memory 52 can store, for example, 64 captured images.

The gripping portion 2 includes a power supply switch 21 which turns on and off the intraoral camera 1 by sliding. The gripping portion 2 includes an imaging button 22 positioned more in the +X direction and playback buttons 23A and 23B positioned more in the −X direction. The user can capture an image of the object by pressing the imaging button 22 with, for example, his or her forefinger while gripping the gripping portion 2. The gripping portion 2 accommodates a battery 24 which supplies power to each unit of the intraoral camera 1.

The external device 300 can be implemented using a display only or a PC (Personal Computer).

Figure 2:
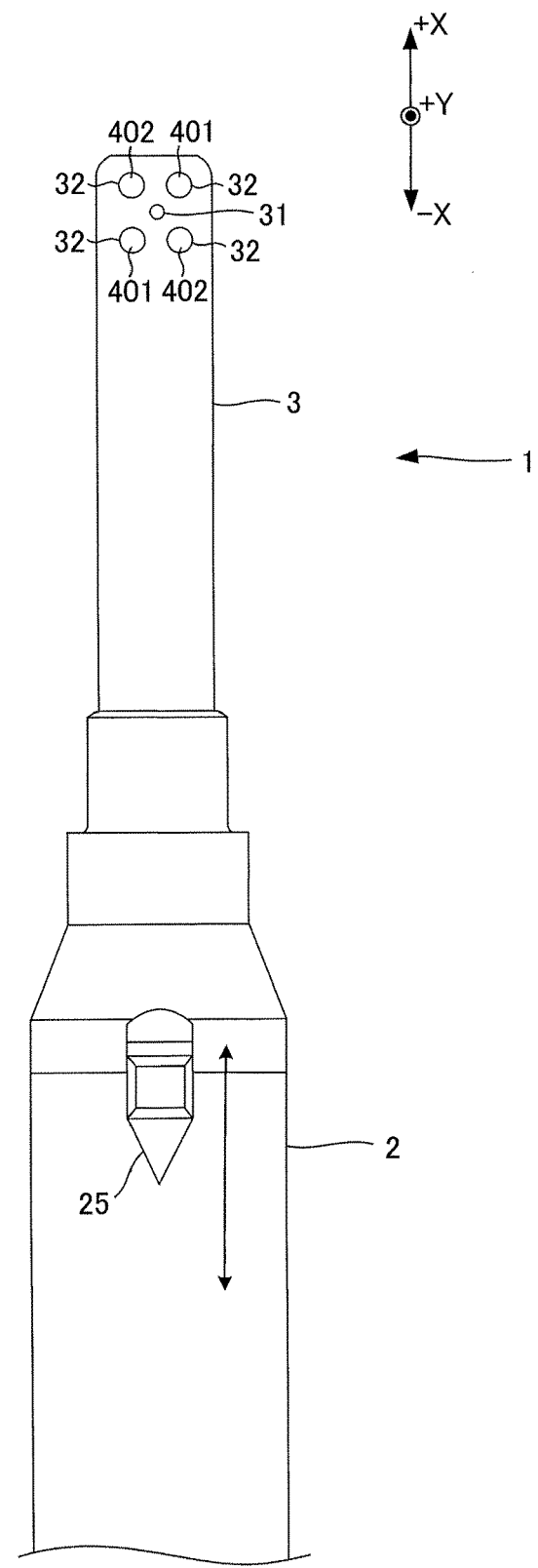
FIG. 2 is a plan view illustrating a surface of the intraoral camera, on which an imaging window is provided.

FIG. 2 is a plan view illustrating a surface of the intraoral camera 1 in the +Y direction, on which the imaging window 31 is provided.

The imaging window 31 is a hole formed at the distal end of the insertion portion 3 in the +X direction. The imaging window 31 is sealed with a transparent film. Light from the object enters the intraoral camera 1 from the imaging window 31.

Four irradiation windows 32 surround the imaging window 31. The irradiation windows 32 allow white LEDs 401 (see FIG. 3) and 405-nm LEDs 402 (see FIG. 3) mounted in the insertion portion 3 to be exposed to the outside. The white LEDs 401 emit high-intensity white light. The 405-nm LEDs 402 emit light in a wavelength range, with 405 nm as its center.

Two white LEDs 401 and two 405-nm LEDs 402 are provided. The pair of white LEDs 401 are opposed to each other across the imaging window 31 on the surface of the insertion portion 3. The pair of 405-nm LEDs 402 are also opposed to each other across the imaging window 31 on the surface of the insertion portion 3. The pairs of white LEDs 401 and 405-nm LEDs 402 are respectively positioned in correspondence with the vertices of a square.

The gripping portion 2 includes a selecting switch 25. In the intraoral camera 1, sliding the selecting switch 25 allows LEDs which illuminate the object to be switched to the white LEDs 401 or the 405-nm LEDs 402.

Figure 3:
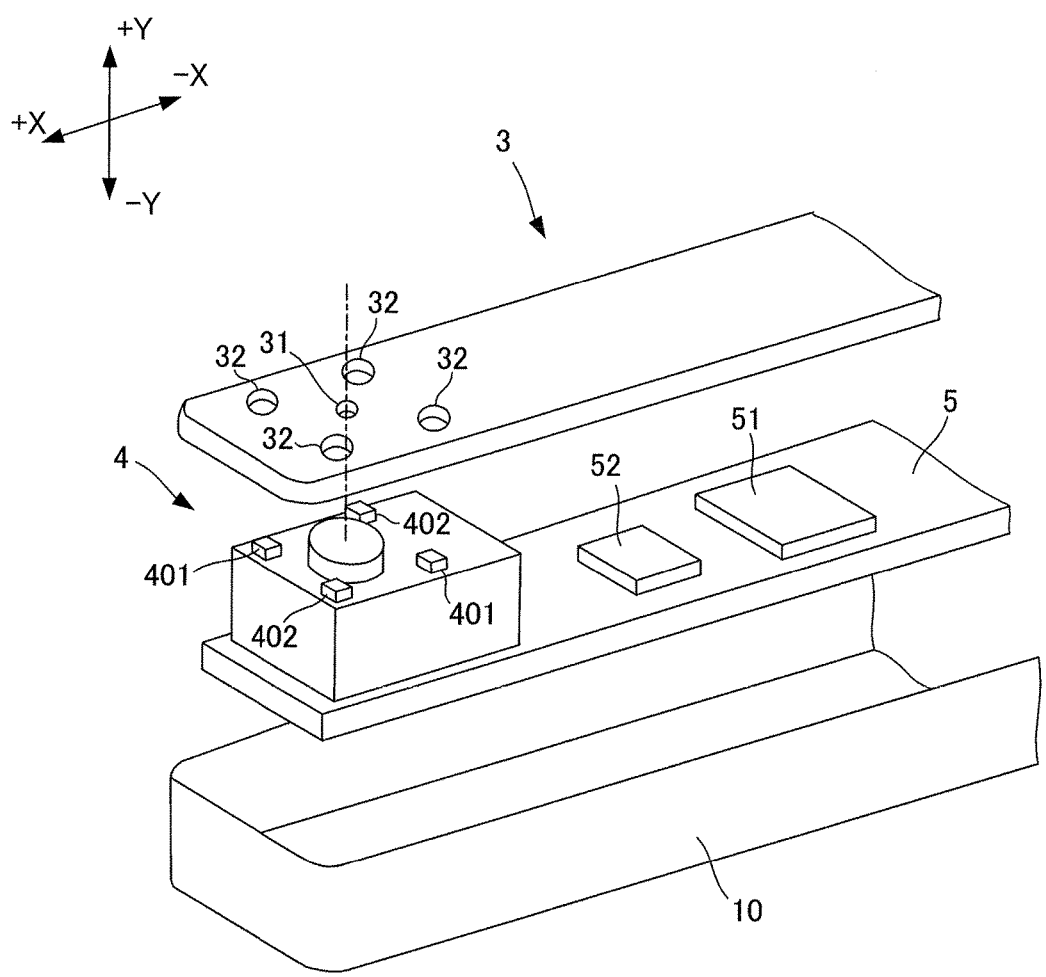
FIG. 3 is a perspective view illustrating a board and an imaging unit.

FIG. 3 is a perspective view illustrating a board 5 and an imaging unit 4.

The board 5 is accommodated in the insertion portion 3. A controller 51, the memory 52, and the imaging unit 4 are mounted on the board 5. The controller 51 controls the overall intraoral camera 1. The imaging unit 4 captures an image of the object via the imaging window 31. The white LEDs 401 and the 405-nm LEDs 402 are mounted on the imaging unit 4. The imaging unit 4 has its optical axis direction coinciding with the Y direction within the distal end of the insertion portion 3 in the X direction.

Figure 4:
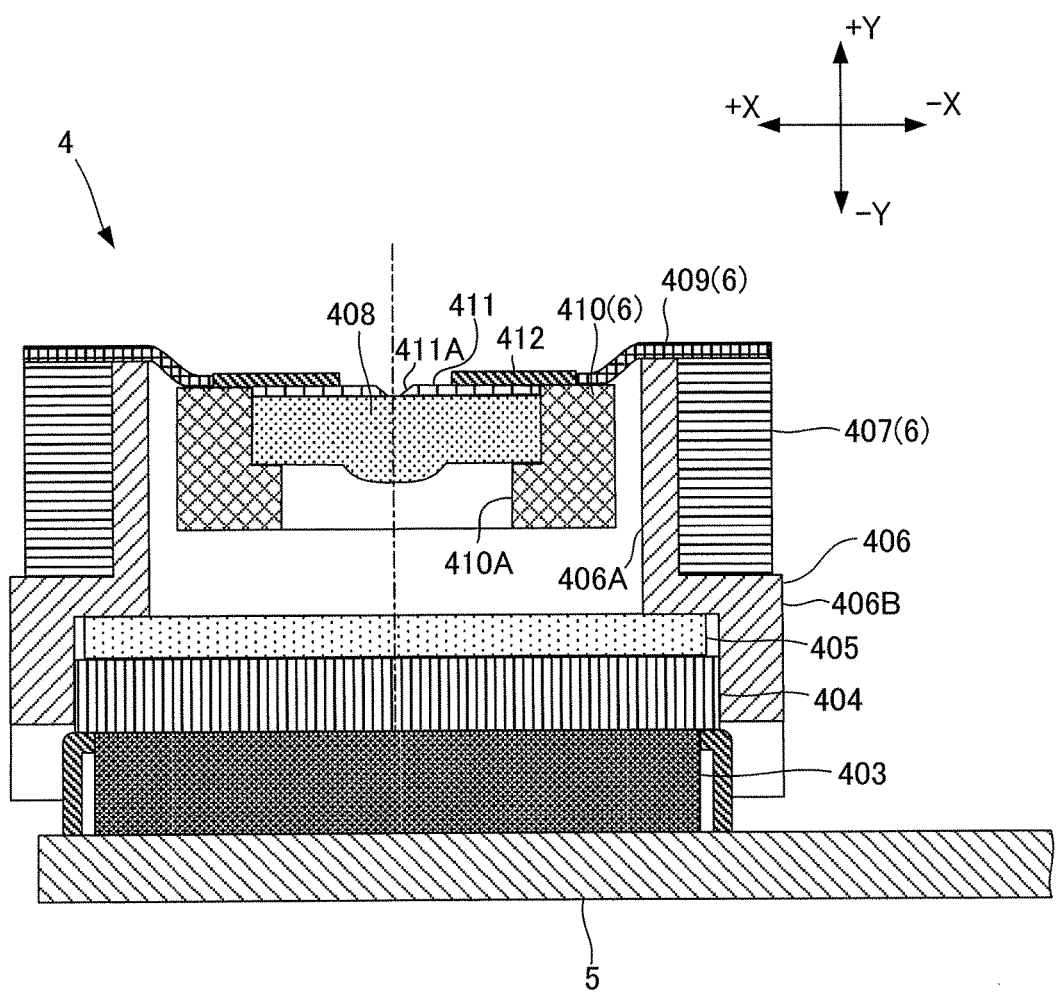
FIG. 4 is a cross-sectional view of the imaging unit.

FIG. 4 is a cross-sectional view of the imaging unit 4. FIG. 4 shows a schematic view for explaining the imaging principle. The white LEDs 401 and the 405-nm LEDs 402, for example, are not illustrated in FIG. 4.

The imaging unit 4 includes an imaging device 403 such as a CCD (Charge Coupled Device) or a CMOS (Complementary Metal Oxide Semiconductor), a low-pass filter 404, a cover glass 405, a holder 406, a coil 407, a focusing lens 408, a vibrating plate 409, a magnet 410, an iris 411, and a holding member 412.

The imaging device 403 is mounted on the board 5. The imaging device 403 captures an object image formed on the imaging device 403 via the focusing lens 408 to obtain a captured image. The captured image is stored in the memory 52. In this embodiment, the frame rate of the imaging device 403 is 30 FPS (Frame Per Second).

The low-pass filter 404 and the cover glass 405 are stacked on the imaging device 403.

The holder 406 has a cylindrical shape. The holder 406 has small- and large-diameter portions 406A and 406B. The large-diameter portion 406B is formed more in the −Y direction than the small-diameter portion 406A and covers the periphery of the imaging device 403.

The coil 407 is wound in an annular shape and positioned outside the small-diameter portion 406A. The coil 407 is located outside the magnet 410 in the radial direction. The magnet 410 supports the focusing lens 408. Supplying power to the coil 407 generates a magnetic force between the coil 407 and the magnet 410 to move the magnet 410 and the focusing lens 408 in the optical axis direction (±Y directions) of the focusing lens 408.

The vibrating plate 409 has an annular shape and has its outer peripheral portion fixed to the end face of the holder 406 in the +Y direction. The end face of the magnet 410 in the +Y direction is fixed to the inner peripheral portion of the vibrating plate 409. The vibrating plate 409 supports the magnet 410 and the focusing lens 408 at a home position in the optical axis direction in a normal state in which no current is supplied to the coil 407.

When a current is supplied to the coil 407 to move the magnet 410 and the focusing lens 408 in the optical axis direction, the vibrating plate 409 applies a restoring force to the magnet 410 and the focusing lens 408 in accordance with the amount of shift of the magnet 410 and focusing lens 408 from the home position in the optical axis direction. The vibrating plate 409 also functions as a guide which moves the magnet 410 and the focusing lens 408 in the optical axis direction.

The magnet 410 has an annular shape and includes an annular flange portion 410A projecting inwards from the distal end portion of its inner peripheral surface in the −Y direction. The magnet 410 accommodates the focusing lens 408 and supports the focusing lens 408 through the flange portion 410A. The magnet 410 is located outside the focusing lens 408 in the radial direction and moves together with the focusing lens 408.

Light from the object within the oral cavity impinges on the focusing lens 408 via the imaging window 31. The focusing lens 408 focuses the light from the object to form an object image on the imaging device 403.

The iris 411 is positioned more to the object side than the focusing lens 408 and narrows the light incident on the focusing lens 408 through an aperture portion 411A.

The holding member 412 extends across the end faces of the iris 411 and magnet 410 in the +Y direction. The holding member 412 and the flange portion 410A of the magnet 410 clamp the focusing lens 408 and the iris 411.

In this embodiment, a lens moving mechanism 6 that moves the focusing lens 408 in the optical axis direction includes the magnet 410, the vibrating plate 409, and the coil 407.

Figure 5:
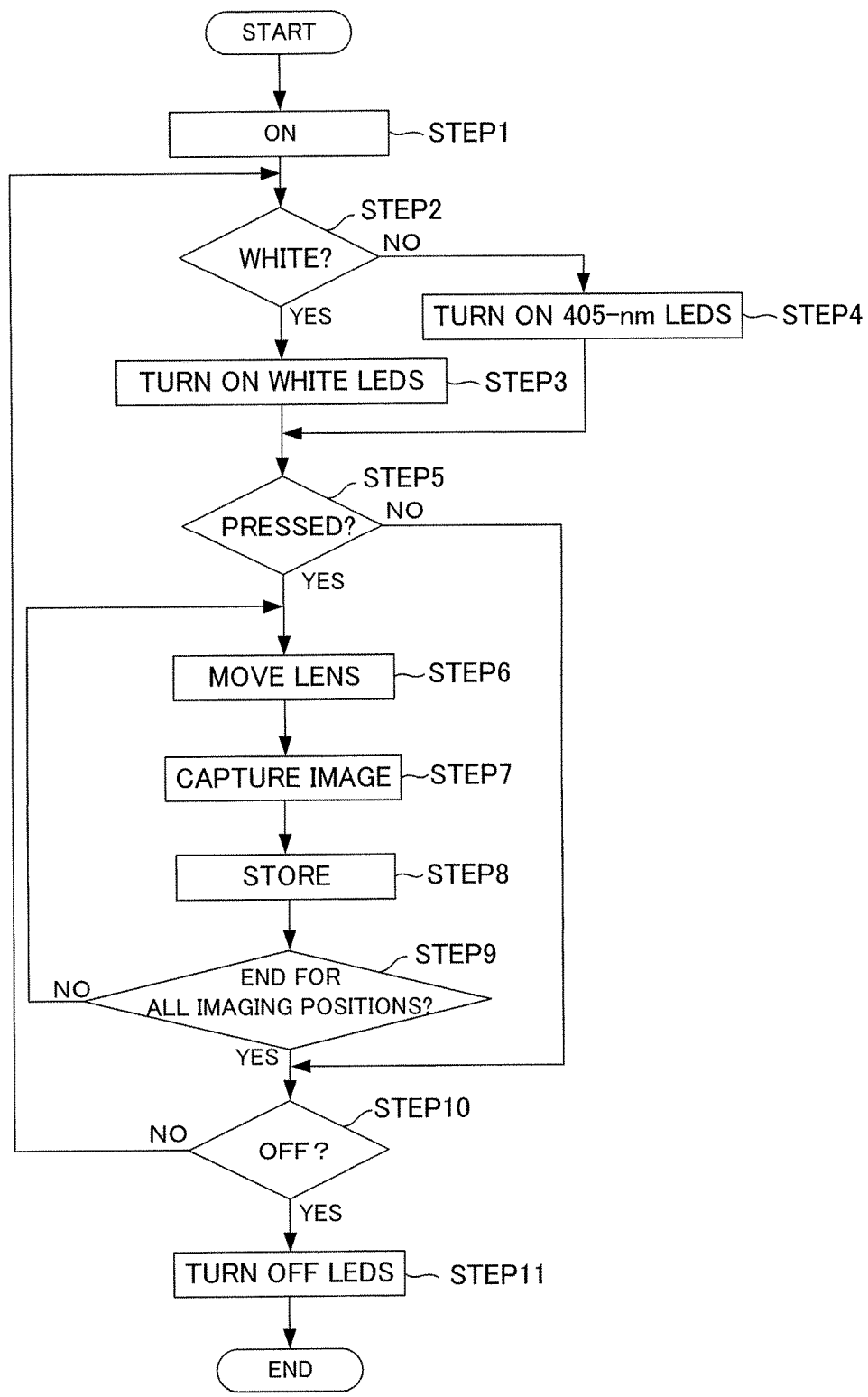
FIG. 5 is a flowchart for explaining the operation of the intraoral camera.

The operation of the intraoral camera 1 will be described below with reference to a flowchart shown in FIG. 5.

When the power supply switch 21 is turned on (STEP 1), if the selecting switch 25 is set at an ON position for the white LEDs 401 (YES in STEP 2), the controller 51 turns on the white LEDs 401 (STEP 3). If the selecting switch 25 is set at an ON position for the 405-nm LEDs 402 (NO in STEP 2), the controller 51 turns on the 405-nm LEDs 402 (STEP 4).

The user operates the intraoral camera 1 to point the imaging window 31 at an object such as a row of teeth to be captured and presses the imaging button 22.

If the imaging button 22 is pressed and an imaging instruction is input (YES in STEP 5), the controller 51 moves the focusing lens 408 to a plurality of imaging positions in the optical axis direction to obtain an image captured when the focusing lens 408 is positioned at each of the imaging positions and store these images in the memory 52 (STEPS 6 to 8). If the imaging button 22 remains to be pressed (NO in STEP 5), the controller 51 stands by unless the power supply switch 21 is turned off (NO in STEP 10) and repeats the process from STEP 2.

Figure 6:
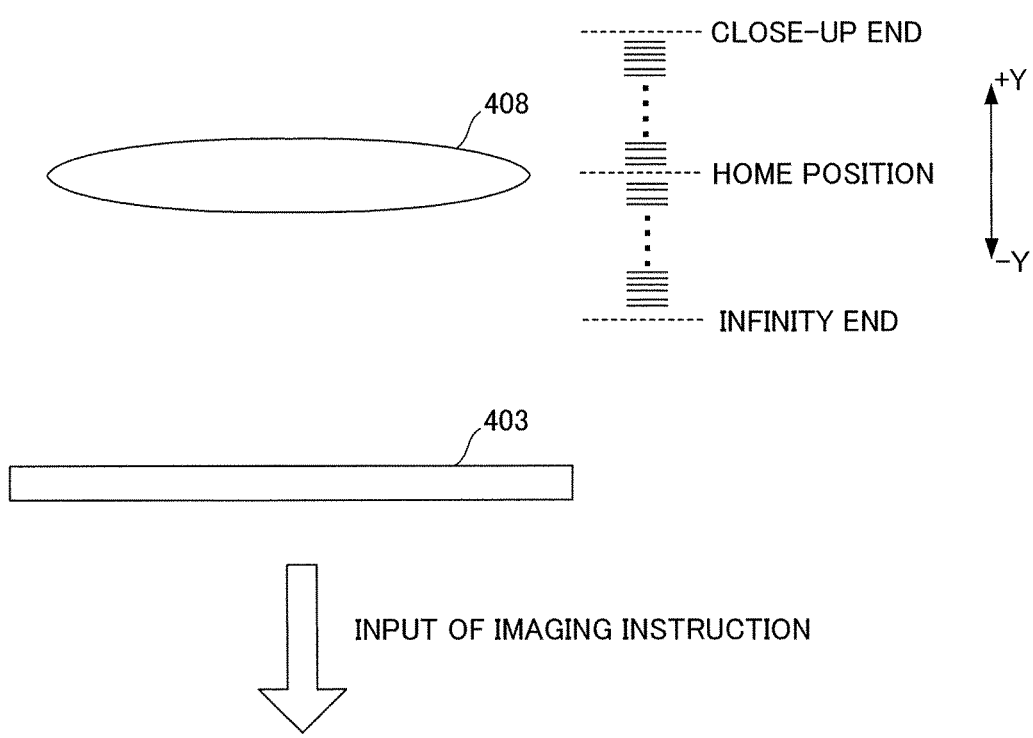
FIG. 6 includes diagrams for explaining one example of a method of moving a focusing lens.
Figure 6:
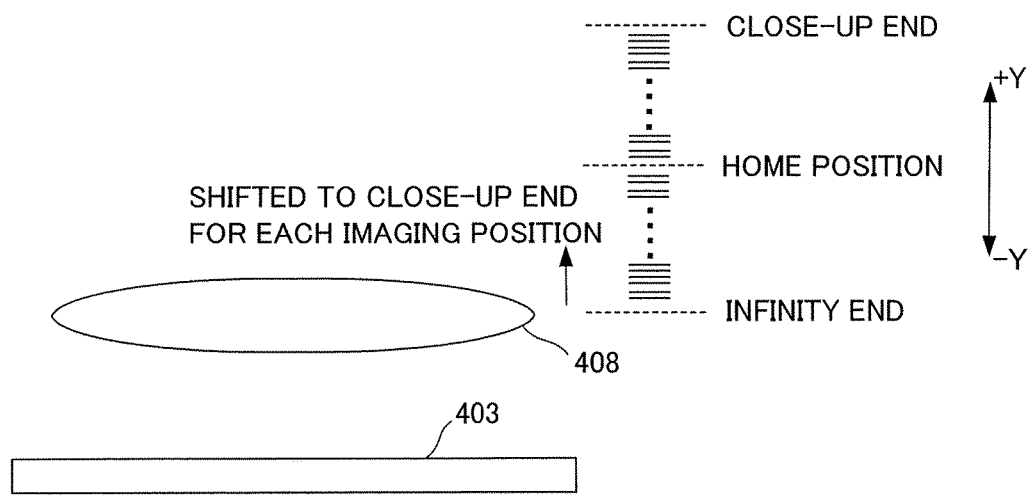

FIG. 6 includes diagrams for explaining an example of a method of moving the focusing lens 408 in imaging. (A) in FIG. 6 is a view illustrating the position of the focusing lens 408 before an imaging instruction is input. (B) in FIG. 6 is a view illustrating the position of the focusing lens 408 immediately after an imaging instruction was input, and a method of moving the focusing lens 408.

In this embodiment, the imaging position changes in 30 stages, the number of which is equal to the frame rate (30 FPS). The imaging position is set to have an almost equal number of stages in the +Y and −Y sides with respect to the home position.

If the imaging button 22 is pressed and an imaging instruction is input (YES in STEP 5), the controller 51 moves the focusing lens 408 to the imaging position at an infinity end of the set imaging positions (STEP 6).

At this time, the controller 51 supplies a current to the coil 407 to make it generate a magnetic force so that the focusing lens 408 moves to the imaging position of the infinity end and stops at this position. The controller 51 changes the amount of current supplied to the coil 407 in accordance with a target imaging position, so that the focusing lens 408 moves to the target imaging position and stops at this position.

The controller 51 moves the focusing lens 408 to the imaging position of the infinity end (STEP 6) before the first imaging operation at the driving timing (30 FPS) of the imaging device 403. The controller 51 then drives the imaging device 403 at the first driving timing of the imaging device 403.

The controller 51 obtains an image of the object captured when the focusing lens 408 is positioned at the imaging position of the infinity end (STEP 7), and stores the captured image in the memory 52 (STEP 8). The controller 51 assigns 1 to metadata of the captured image as a position number indicating that the focusing lens 408 is positioned at the imaging position of the infinity end.

Since imaging has not ended for all the imaging positions (NO in STEP 9), the controller 51 moves the focusing lens 408 from the imaging position of the infinity end to the close-up end side by one stage (STEP 6) before the second imaging operation at the driving timing (30 FPS) of the imaging device 403.

The controller 51 obtains a captured image (STEP 7) and stores it in the memory 52 (STEP 8). The controller 51 assigns 2 to metadata of the captured image as a position number indicating that the focusing lens 408 is positioned more to the close-up end side than the imaging position of the infinity end by one stage.

The controller 51 changes the amount of current supplied to the coil 407, stepwise in accordance with the driving timing of the imaging device 403 to move the focusing lens 408. The controller 51 obtains captured images while shifting the focusing lens 408 from the infinity end side to the close-up end side for each stage by stages, the number of which is equal to the frame rate, and stores them in the memory 52 (STEPS 6 to 9).

The controller 51 assigns the image captured at each of the imaging positions with a position number corresponding to the imaging position of the focusing lens 408 as metadata, that is, assigns these images with position numbers 1 to 30 corresponding to the frame rate (30 FPS) (STEP 8).

When imaging has ended for all the imaging positions (YES in STEP 9), the controller 51 returns the focusing lens 408 to the home position and assumes a standby state (NO in STEP 10), and then repeats the process from STEP 2. If the power supply switch 21 is turned off (YES in STEP 10), the controller 51 turns off the white LEDs 401 or the 405-nm LEDs 402 that are kept ON (STEP 11) and ends the process.

If the external device 300 is implemented using a display only, the intraoral camera 1 transmits the captured images stored in the memory 52 to the external device 300 to allow the external device 300 to play them back every time the playback buttons 23A and 23B (see FIG. 1) are pressed. Images corresponding to 30 frames captured at different imaging positions are stored in the memory 52 for each imaging operation upon one pressing operation of the imaging button 22.

The user can change the captured image displayed on the external device 300 to the image captured one frame before the current image by pressing the playback button 23A (see FIG. 1) or to the image captured one frame after the current image by pressing the playback button 23B (see FIG. 1). The external device 300 may simultaneously display the captured images and the position numbers assigned to these images.

As described above, by operating the playback buttons 23A and 23B, the user can select an in-focus captured image from the captured images of the object corresponding to 30 frames obtained by one pressing operation of the imaging button 22 and display it on the external device 300.

If the external device 300 is implemented using a PC, the external device 300 can not only play back the captured images in the intraoral camera 1 but also read the captured images from the memory 52 of the intraoral camera 1 and store and manage them. For example, the external device 300 may read captured images of the object corresponding to 30 frames every time the intraoral camera 1 obtains these images. The external device 300 may simultaneously display the captured images and the position numbers assigned to these images. The user may select and store an in-focus image in the external device 300.

(Effects)

The intraoral camera 1 is limited in size because of its use within the oral cavity. Therefore, mounting an autofocus mechanism in the intraoral camera 1 imposes strict constraints in terms of the size and arrangement of optical components of the autofocus mechanism. Furthermore, the intraoral camera 1 is used under very dark intraoral environments and requires a wide range of imaging distance to the object because, for example, images of a row of teeth are captured close-up or from far away.

Mounting an autofocus mechanism in the intraoral camera 1 imposes strict constraints in terms of the size and arrangement of optical components of the autofocus mechanism. Moreover, the intraoral camera 1 is used under environments readily influenced by the illumination state of light illuminating the object due to an insufficient amount of light. It is therefore difficult for the autofocus mechanism to achieve highly accurate focusing.

To solve the above-mentioned problems, in this embodiment, an autofocus mechanism is intentionally omitted. Instead, every time an imaging instruction is input, the focusing lens 408 is moved to a plurality of imaging positions in the optical axis direction to obtain captured images. In this embodiment, therefore, it is possible to reliably obtain an in-focus image.

In the conventional intraoral camera 1 that uses an autofocus mechanism, the autofocus mechanism cannot be placed in the insertion portion 3 and must be placed in the gripping portion 2 in terms of its size. Hence, the conventional intraoral camera 1 cannot be equipped with the battery 24 and therefore must be connected to an external power supply by wiring. The intraoral camera 1 performs precise operations and thus may be hard to use in the presence of wiring. As another problem, the conventional optical system for imaging includes an autofocus mechanism and is therefore heavy, as described in "BACKGROUND OF THE INVENTION."

The use of an autofocus mechanism requires arranging, in the insertion portion 3, optical components for guiding light received from the imaging window 31 of the insertion portion 3 to the autofocus mechanism in the gripping portion 2 and the imaging device 403. In this embodiment, an autofocus mechanism is omitted. This makes it possible to place the imaging unit 4 at the distal end portion of the intraoral camera 1 and obviates the need for the optical components. In this embodiment, therefore, it is possible to obviate the need for the optical components and an autofocus mechanism and provide a compact, lightweight optical system for imaging (imaging unit 4).

The controller 51 changes the value of current supplied to the coil 407 stepwise in accordance with the driving timing of the imaging device 403, to thereby allow the focusing lens 408 to move at high speed to a plurality of imaging positions between the infinity and close-up ends.

In this embodiment, since the imaging unit 4 can be positioned at the distal end portion of the intraoral camera 1, the battery 24 can be positioned in the gripping portion 2 to attain wireless communication by the intraoral camera 1.

As described above, in this embodiment, miniaturization and reduction in weight of an optical system for imaging and wireless communication for an intraoral camera 1 are simultaneously achieved.

Assume that in the imaging unit 4, the coil 407 is fixed to the focusing lens 408 and the magnet 410 is fixed to the holder 406, in contrast to the configuration according to this embodiment. Then, the coil 407 must be wired into the holder 406 from the outside of the holder 406. This complicates the structure of the imaging unit 4 and increases the cost.

In this embodiment, since the coil 407 is fixed to the holder 406 and the magnet 410 is fixed to the focusing lens 408, the coil 407 need not be wired into the holder 406. This can simplify the structure of the imaging unit 4 and reduce the cost in this embodiment.

In this embodiment, the imaging position changes in stages, the number of which is equal to the frame rate of the imaging device 403. This simultaneously achieves setting of a number of stages of the imaging position sufficient to obtain an in-focus image and shortening of the imaging time taken for one pressing operation of the imaging button 22.

In this embodiment, since position numbers corresponding to the imaging positions of the focusing lens 408 are assigned to the captured images as metadata, these images can be easily managed.

(Second Embodiment)

Figure 7:
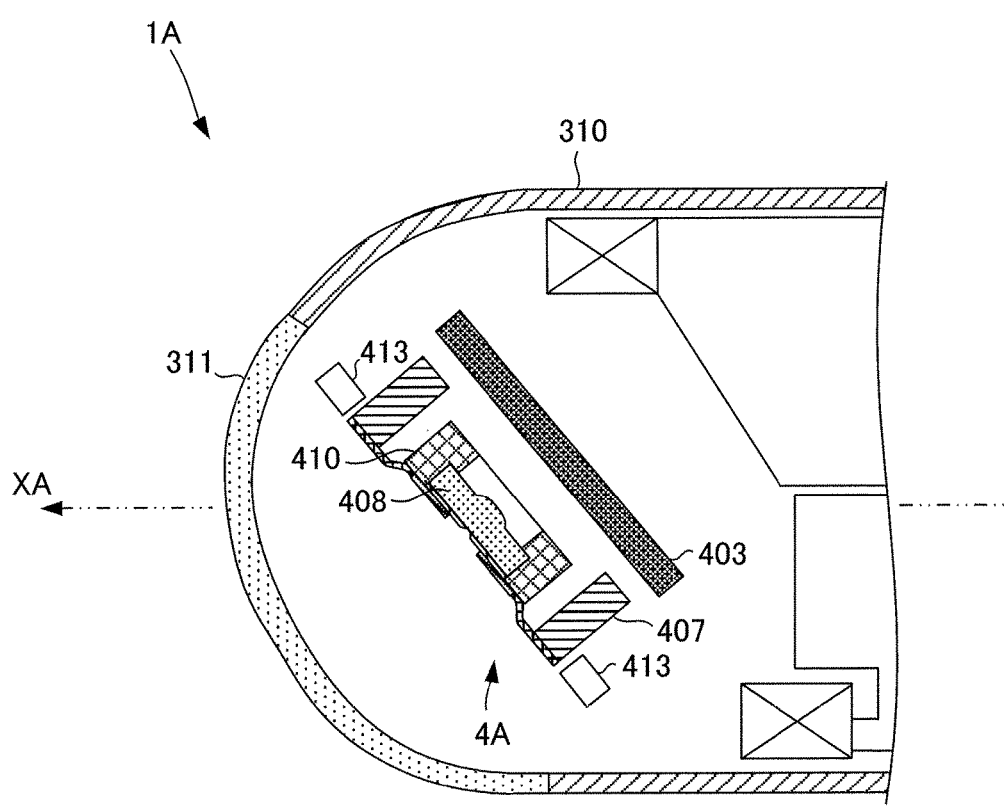
FIG. 7 is a cross-sectional view illustrating an example of a capsule endoscope to which an imaging apparatus according to the present invention is applied.

FIG. 7 is a cross-sectional view illustrating an example of a capsule endoscope 1A to which an imaging apparatus according to the present invention is applied.

In the capsule endoscope 1A, a case 310 extends in the horizontal direction of FIG. 7 and has a central axis XA. The case 310 includes, at its distal end, a transparent portion 311 which transmits light. The case 310 accommodates an imaging unit 4A opposed to the transparent portion 311. The imaging unit 4A is oriented so that the optical axis of a focusing lens 408 is tilted with respect to the central axis XA.

The imaging unit 4A includes a plurality of LEDs 413 which emit light beams having different wavelengths, the focusing lens 408, a magnet 410, a coil 407, and an imaging device 403, as in the first embodiment.

The capsule endoscope 1A moves in a living body while the imaging unit 4A is assuming an attitude that enables imaging of objects seen ahead in the moving direction. The capsule endoscope 1A is pushed forwards in the moving direction by small intestinal peristalsis while being in press contact with, for example, the wall surface of the small intestine.

Electromagnetic energy is sent from the outside of the living body to the capsule endoscope 1A. Upon receiving the electromagnetic energy from the outside of the living body by a power-generating magnetism receiving coil (not shown), the capsule endoscope 1A causes the coil to generate and supply power to, for example, a controller (not shown) and the imaging unit 4A.

The capsule endoscope 1A has three rotor coils (not shown) arranged at intervals of 60° with the central axis XA as its center. When the user wears a vest embedded with three stator coils, the three stator coils are set outside the living body. Controlling the rotor coils in the capsule endoscope 1A and the stator coils outside the living body makes it possible to circumferentially rotate the imaging direction with respect to the moving direction (central axis XA).

As described above, the capsule endoscope 1A circumferentially rotates the imaging direction and continuously captures images while moving in, for example, the small intestine. The capsule endoscope 1A obtains captured images while shifting the imaging position of the focusing lens 408 from the close-up end side to the infinity end side for each frame rate, as in the first embodiment. In this embodiment, the capsule endoscope 1A has no memory and transmits the captured images to an external device via a transmitter (not shown). Hence, an in-focus captured image can be selected and used for, for example, medical diagnosis on the external device.

(Third Embodiment)

Figure 8:
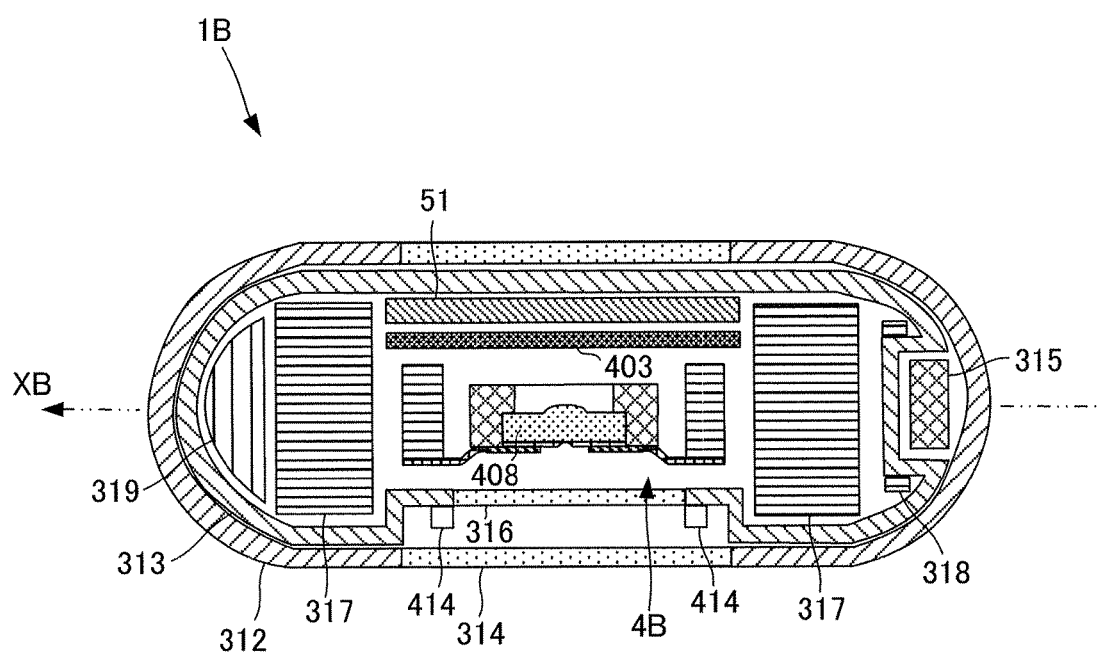
FIG. 8 is a cross-sectional view illustrating another example of a capsule endoscope to which the imaging apparatus according to the present invention is applied.

FIG. 8 is a cross-sectional view illustrating an example of a capsule endoscope 1B to which an imaging apparatus according to the present invention is applied.

The capsule endoscope 1B has a double-case structure and includes an outer case 312 and an inner case 313 positioned inside the outer case 312. The inner case 313 can rotate about a central axis XB. The outer case 312 has, at its longitudinal central portion, a transparent portion 314 formed over the entire circumferential length. The inner case 313 has, at its longitudinal central portion, a transparent portion 316 as well. A plurality of LEDs 414 which emit light beams having different wavelengths surround the transparent portion 316. A magnet 315 is provided on the side of one end in the outer case 312.

An imaging unit 4B is opposed to the transparent portion 316 in the inner case 313 and captures images of the interior walls of, for example, a small intestine via the transparent portions 316 and 314. A controller 51 is provided on the back side of an imaging device 403 of the imaging unit 4B. In the inner case 313, a power-generating magnetism receiving coil 317 is positioned so that the imaging unit 4B is interposed therebetween along the central axis XB. An attitude control coil 318 surrounds the magnet 315 on the side of one end in the inner case 313, and a transmitter 319 is provided on the side of the other end in the inner case 313.

Upon receiving electromagnetic energy from the outside of the living body by the power-generating magnetism receiving coil 317, the capsule endoscope 1B causes the coil to generate and supply power to the attitude control coil 318, to thereby rotate the inner case 313 about the central axis XB by interaction with the magnet 315 and circumferentially rotate the imaging direction with respect to the moving direction (central axis XB).

The capsule endoscope 1B circumferentially rotates the imaging direction and continuously captures images while moving in, for example, the small intestine. The capsule endoscope 1B obtains captured images while shifting the imaging position of the focusing lens 408 from the close-up end side to the infinity end side for each frame rate, as in the first and second embodiments. The capsule endoscope 1B transmits the captured images to an external device via the transmitter 319.

(Fourth Embodiment)

Figure 9:
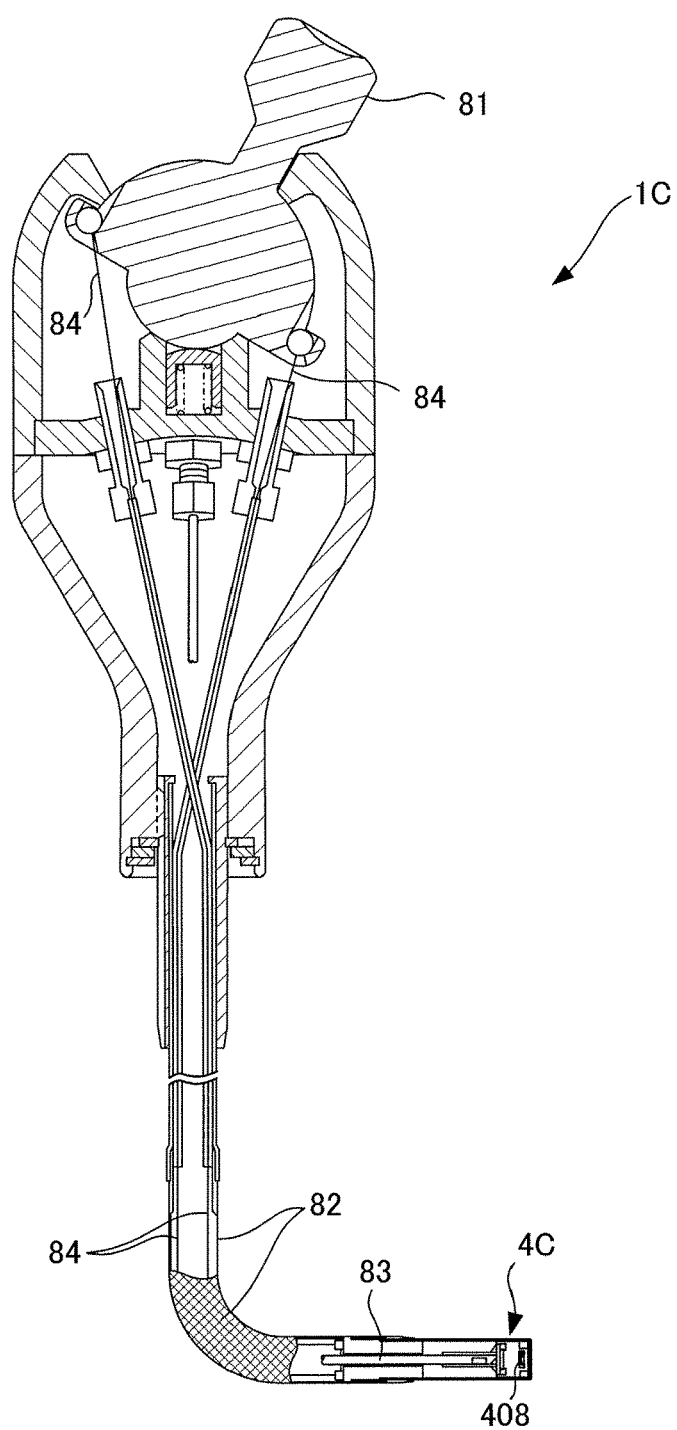
FIG. 9 is a cross-sectional view illustrating an example of a joystick endoscope to which the imaging apparatus according to the present invention is applied.

FIG. 9 is a cross-sectional view illustrating an example of a joystick endoscope 1C to which an imaging apparatus according to the present invention is applied.

The joystick endoscope 1C is used to capture images of objects at sites hard to capture, including the interiors of narrow tubes and a body. Since the basic structure of the joystick endoscope 1C is the same as that described in Japanese Patent Application Laid-Open No. 2009-89955, a brief description thereof will be given herein.

A pivotally movable operation member 81 is provided at one end of the joystick endoscope 1C and a bendable hollow pipe member 82 is provided at its other end. An imaging unit 4C as in the first to third embodiments is provided at the distal end of the pipe member 82. The imaging unit 4C captures an image of an object seen in the direction in which the pipe member 82 is pointed. The imaging unit 4C is connected to a controller (not shown) by wiring 83. Since the operation member 81 is connected to the pipe member 82 via a plurality of wires 84, pivoting the operation member 81 makes it possible to bend the pipe member 82 in an appropriate direction and operate the imaging direction.

The joystick endoscope 1C obtains captured images while shifting the imaging position of a focusing lens 408 of the imaging unit 4C from the close-up end side to the infinity end side for each frame rate, as in the first to third embodiments. The joystick endoscope 1C may store the obtained, captured images in a memory to play them back on an external device, as in the first embodiment. Alternatively, the joystick endoscope 1C may transmit the captured images to an external device, as in the second and third embodiments.

Although the joystick endoscope 1C is used in this embodiment, an endoscope having another structure can also be used. That is, an imaging unit 4C as in this embodiment can be positioned at the distal end of the elongated pipe member 82.

(Modification)

The imaging position of the focusing lens 408 may be moved for each stage from the close-up end to the infinity end. The imaging position may be set only in one of the +Y- and −Y directions from the home position. The distance between two imaging positions adjacent in the optical axis direction may be different or equal. The home position can be set to an arbitrary imaging position ranging between the infinity and close-up ends. For example, the home position can be set to the infinity or close-up end.

A plurality of captured images can also be obtained at a predetermined imaging position by a plurality of imaging operations without changing the imaging position. In this case, the number of imaging positions to which the focusing lens 408 is moved is smaller than the number of the frame rate. Although a position number corresponding to the imaging position is assigned to a plurality of captured images obtained at the same imaging position, different position numbers can also be assigned to distinguish a plurality of captured images obtained at the same imaging position from each other.

In obtaining a plurality of captured images at a predetermined imaging position, the number of captured images may be equal or different for all imaging positions. When the number of captured images is set equal for all imaging positions, the number of stages of the imaging position can be set to a value obtained by dividing the frame rate (30 FPS) by an integer of 2 or more. The number of stages of the imaging position can be set to, for example, 10 obtained by dividing the frame rate (30 FPS) by 3.

A plurality of captured images can be continuously played back in the order (ascending or descending order) of position number on the external device 300. Thus, the user can continuously confirm a plurality of captured images on the external device 300 and easily select an in-focus captured image. When an in-focus captured image is selected and a position number corresponding to this image is input to the external device 300, the selected, captured image can be confirmed again.

When a plurality of captured images are obtained at a predetermined imaging position, and input of a position number is accepted, the external device 300 can simultaneously display a plurality of captured images corresponding to the input position number.

The controller 51 may determine a captured image having a highest frequency component of the captured images as an in-focus captured image, and assign metadata indicating a best-focus image to this image. The controller 51 may store only the best-focus captured image in the memory 52 or display it on the external device 300.

When a best-focus image is specified, the controller 51 can specify the distance from the focusing lens 408 to the object, on the basis of the imaging position corresponding to the best-focus captured image. More specifically, the distance from the focusing lens 408 to the object can be specified on the basis of the focal length of the focusing lens 408 and the distance from the focusing lens 408 to the imaging device (imaging plane) 403 which is specified from the imaging position. Note that as long as the relationship between the imaging position and the amount of power supplied to the coil 407 is obtained in advance, the imaging position, that is, the distance from the focusing lens 408 to the imaging device 403 can be specified by detecting the amount of power supplied to the coil 407. The controller 51 can display the distance from the focusing lens 408 to the object on the external device 300. Thus, the user can determine the position of the intraoral camera 1 or an imaging apparatus according to the present invention, represented by an endoscope such as the joystick endoscope 1C described in Embodiment 4, with respect to an object in capturing an image of the object using the intraoral camera 1 or the imaging apparatus.

In the imaging unit 4, the coil 407 may be fixed to the focusing lens 408 and the magnet 410 may be fixed to the holder 406.

The intraoral camera 1 need not always include the battery 24 and may be connected to an external power supply by wiring.

REFERENCE SIGNS LIST

1: intraoral camera (imaging apparatus)
6: lens moving mechanism (moving mechanism)
10: case
51: controller
52: memory
403: imaging device
407: coil
408: focusing lens (lens)
409: vibrating plate
410: magnet

What is claimed is:

1. An imaging apparatus comprising:
a lens that focuses light from an object;
a moving mechanism that moves the lens in an optical axis direction;
an imaging device that captures an image of the object formed by the lens to obtain a captured image; and
a controller for driving, in response to an input of an imaging instruction, the moving mechanism to move the lens to a plurality of imaging positions from one of an infinity end to a close-up end, and driving the imaging device when the lens is positioned at each of the plurality of imaging positions, the controller obtaining captured images captured at each of the plurality of imaging positions for display on a display unit,
wherein the moving mechanism comprises:
a magnet that moves together with the lens and has an annular shape, the magnet including a housing portion for housing the lens inside and a flange portion that projects inward from the inside of the housing portion and supports the lens;
a vibrating plate that supports the magnet and the lens, and generates a restoring force in a direction to return the magnet and the lens to a home position in accordance with an amount of shift of the magnet and the lens from the home position in the optical axis direction; and
a coil that is located outside the magnet in the radial direction and generates a magnetic force to move the magnet and the lens in the optical axis direction when power is supplied to the coil, and
the controller changes an amount of power supplied to the coil to move the magnet and the lens to the plurality of imaging positions.

2. The imaging apparatus according to claim 1, wherein the controller moves the lens to the plurality of imaging positions, the number of which is equal to a frame rate of the imaging device, from one of the infinity end to the close-up end in response to the input of the imaging instruction.

3. The imaging apparatus according to claim 2, further comprising a memory that stores the image captured when the lens is positioned at each of the plurality of imaging positions, and
the controller assigns, as metadata, a number corresponding to an imaging position of the lens to an image captured at each of the plurality of imaging positions.

4. The imaging apparatus according to claim 1, further comprising a memory that stores the image captured when the lens is positioned at each of the plurality of imaging positions, and
the controller assigns, as metadata, a number corresponding to an imaging position of the lens to an image captured at each of the plurality of imaging positions.

5. The imaging apparatus according to claim 1, further comprising:

an iris provided on an incident surface of the lens that reduces incident light to the lens; and a holding member provided on an end face of the magnet away from the imaging device that clamps the lens and the iris to the flange portion, wherein one end of the vibrating plate is secured to the end face of the magnet.

6. The imaging apparatus according to claim 5, wherein the incident surface is flat and an emitting surface of the lens has a convex surface.

7. The imaging apparatus according to claim 6, wherein the iris directly contacts the incident surface.

8. An intraoral camera comprising:
a lens that focuses light from an object;
a moving mechanism that moves the lens in an optical axis direction;
an imaging device that captures an image of the object formed by the lens to obtain a captured image;
a memory for storing the captured image;
a controller for driving, in response to an input of an imaging instruction, the moving mechanism to move the lens to a plurality of imaging positions from one of an infinity end to a close-up end and stores, in the memory, captured images captured at each of the plurality of imaging positions for display on a display unit; and
a case that extends in a first direction, for accommodating the lens, the moving mechanism, the imaging device, the memory, and the controller,
wherein the lens, the moving mechanism, and the imaging device are arranged to match the optical axis direction with a direction perpendicular to the first direction within a distal end of the case, and
the moving mechanism comprises:
a magnet that moves together with the lens and has an annular shape, the magnet including a housing portion for housing the lens inside and a flange portion that projects inward from the inside of the housing portion and supports the lens;
a vibrating plate that supports the magnet and the lens, and generates a restoring force in a direction to return the magnet and the lens to a home position in accordance with an amount of shift of the magnet and the lens from the home position in the optical axis direction; and
a coil that is located outside the magnet in the radial direction and generates a magnetic force to move the magnet and the lens in the optical axis direction when power is supplied to the coil, and
the controller changes an amount of power supplied to the coil to move the magnet and the lens to the plurality of imaging positions.

9. The intraoral camera according to claim 8, further comprising:
an iris provided on an incident surface of the lens that reduces incident light to the lens; and
a holding member provided on an end face of the magnet away from the imaging device that clamps the lens and the iris to the flange portion,
wherein one end of the vibrating plate is secured to the end face of the magnet.

10. The intraoral camera according to claim 9, wherein the incident surface is flat and an emitting surface of the lens has a convex surface.

11. The intraoral camera according to claim 10, wherein the iris directly contacts the incident surface.

12. An intraoral camera comprising:
a lens that focuses light from an object;
a moving mechanism that moves the lens in an optical axis direction;
an imaging device that captures an image of the object formed by the lens to obtain a captured image;
a memory for storing the captured image;
a battery;
a controller for driving, in response to an input of an imaging instruction, the moving mechanism to move the lens to a plurality of imaging positions from one of an infinity end to a close-up end and stores, in the memory, captured images captured at each imaging positions for display on a display unit; and
a case that extends in a first direction, for accommodating the lens, the moving mechanism, the imaging device, the memory, the battery, and the controller, the case including a gripping portion gripped by a user and an insertion portion that extends from one end of the gripping portion and is narrower than the gripping portion, and a distal end portion of the insertion portion is inserted in a first direction into an oral cavity,
wherein the battery is arranged inside the gripping portion, and
the lens, the moving mechanism, and the imaging device are arranged to match the optical axis direction with a direction perpendicular to the first direction within the distal end of the insertion portion.

13. The intraoral camera according to claim 12, wherein the controller moves the lens to the plurality of imaging positions, the number of which is equal to a frame rate of the imaging device, from the one of the infinity end to the close-up end in response to the input of the imaging instruction.

14. The intraoral camera according to claim 12, further comprising an iris provided on an incident surface of the lens that reduces incident light to the lens; and
a holding member provided on an end face of the magnet away from the imaging device that clamps the lens and the iris to a flange portion,
wherein one end of a vibrating plate is secured on the end face of the magnet.

15. The intraoral camera according to claim 14, the incident surface is flat and an emitting surface of the lens has a convex surface.

16. The intraoral camera according to claim 15, wherein the iris directly contacts the incident surface.

* * * * *